United States Patent
Zurlo et al.

(10) Patent No.: US 11,760,778 B2
(45) Date of Patent: Sep. 19, 2023

(54) COMPOSITIONS AND METHODS FOR HIGH EFFICIENCY PROTEIN PRECIPITATION

(71) Applicant: PLASMA TECHNOLOGIES, LLC, Charleston, SC (US)

(72) Inventors: Eugene Zurlo, Charleston, SC (US); Dennis Curtin, Plattsburgh, NY (US); Peter Radtke, Charleston, SC (US); Kurt L. Brillhart, Mission Viejo, CA (US)

(73) Assignee: Plasma Technologies, LLC, Charleston, SC (US)

( * ) Notice: Subject to any disclaimer, the term of this patent is extended or adjusted under 35 U.S.C. 154(b) by 421 days.

(21) Appl. No.: 17/030,036

(22) Filed: Sep. 23, 2020

(65) Prior Publication Data
US 2021/0087228 A1    Mar. 25, 2021

Related U.S. Application Data

(63) Continuation of application No. 16/738,932, filed on Jan. 9, 2020, now Pat. No. 10,815,270.
(Continued)

(51) Int. Cl.
*C07K 1/30* (2006.01)
*C07K 1/34* (2006.01)
(Continued)

(52) U.S. Cl.
CPC ............... *C07K 1/30* (2013.01); *C07K 1/303* (2013.01); *C07K 1/34* (2013.01); *C07K 1/36* (2013.01);
(Continued)

(58) Field of Classification Search
CPC . C07K 1/18; C07K 1/30; C07K 1/303; C07K 1/34; C07K 1/36; G01N 30/06;
(Continued)

(56) References Cited

U.S. PATENT DOCUMENTS

| | | |
|---|---|---|
| 2,390,074 A | 12/1945 | Cohn |
| 4,404,132 A | 9/1983 | Mitra |

(Continued)

FOREIGN PATENT DOCUMENTS

| | | |
|---|---|---|
| EP | 0440483 | 8/1991 |
| EP | 2823714 | 1/2015 |

(Continued)

OTHER PUBLICATIONS

Schilcher, Gernot; et al. "Trisodium citrate induced protein precipitation in haemodialysis catheters might cause pulmonary embolism," Clinical Division of Nephrology, Department of Internal Medicine, Medical University of Graz, Graz, Austria. 2012. 5 pages.
(Continued)

*Primary Examiner* — John Kim
(74) *Attorney, Agent, or Firm* — Fish IP Law, LLP

(57) ABSTRACT

Methods for isolating proteins from solution by precipitation and compositions generated thereby are provided. A non-volatile precipitation agent is added to an aqueous protein solution at a low concentration. Water is then removed from the resulting solution until the precipitant and the protein content of the solution increase to a concentration that provides the desired segregation of proteins between supernatant and precipitate. Additional water can be removed from the supernatant to provide additional fractionation. Water can be removed by evaporation (e.g. under reduced pressure) and/or diafiltration.

8 Claims, 2 Drawing Sheets

Related U.S. Application Data

(60) Provisional application No. 62/903,644, filed on Sep. 20, 2019.

(51) Int. Cl.

| | | |
|---|---|---|
| *C07K 1/36* | (2006.01) | |
| *G01N 1/40* | (2006.01) | |
| *G01N 30/06* | (2006.01) | |
| *G01N 30/12* | (2006.01) | |
| *G01N 33/49* | (2006.01) | |
| *C07K 1/18* | (2006.01) | |
| *B01D 15/38* | (2006.01) | |
| *B01D 15/36* | (2006.01) | |

(52) U.S. Cl.
CPC .............. *G01N 1/40* (2013.01); *G01N 1/4055* (2013.01); *G01N 30/06* (2013.01); *G01N 30/12* (2013.01); *G01N 33/491* (2013.01); *B01D 15/361* (2013.01); *B01D 15/38* (2013.01); *C07K 1/18* (2013.01)

(58) Field of Classification Search
CPC ........ G01N 30/12; G01N 33/491; G01N 1/40; G01N 1/4055; B01D 15/08; B01D 15/361; B01D 15/38
See application file for complete search history.

(56) References Cited

U.S. PATENT DOCUMENTS

| | | | |
|---|---|---|---|
| 4,486,282 A | 12/1984 | Bier | |
| 4,697,003 A | 9/1987 | Coan | |
| 4,814,435 A | 3/1989 | Schwarz | |
| 5,177,194 A | 1/1993 | Samo | |
| 5,817,765 A * | 10/1998 | Isaksson | C07K 1/303 |
| | | | 530/394 |
| 6,402,913 B1 | 6/2002 | Gilbert | |
| 6,485,932 B1 | 11/2002 | McIntosh | |
| 6,541,518 B2 | 4/2003 | Shanbrom | |
| 6,835,379 B2 | 12/2004 | Andersson | |
| 6,955,917 B2 | 10/2005 | Mred | |
| 7,297,716 B2 | 11/2007 | Shanbrom | |
| 7,879,331 B2 | 2/2011 | Zurlo | |
| 7,879,332 B2 | 2/2011 | Zurlo | |
| 8,063,189 B2 | 11/2011 | Arunakumar | |
| 8,293,242 B2 | 10/2012 | Zurlo | |
| 9,624,262 B2 | 4/2017 | Van Alstine | |
| 2002/0151688 A1 | 10/2002 | Ristol Debart | |
| 2003/0022149 A1 | 1/2003 | Shanbrom | |
| 2003/0129167 A1 | 7/2003 | Shanbrom | |
| 2006/0223988 A1 | 10/2006 | Maurer | |
| 2009/0292114 A1 | 11/2009 | Kumpalume | |
| 2011/0091992 A1 * | 4/2011 | Dall'Acqua | C07K 16/00 |
| | | | 703/11 |
| 2011/0152503 A1 | 6/2011 | Zurlo | |
| 2011/0237781 A1 | 9/2011 | Lebing | |

FOREIGN PATENT DOCUMENTS

| | | |
|---|---|---|
| WO | 02087560 | 11/2002 |
| WO | 2007030244 | 3/2007 |
| WO | 2017066683 | 4/2017 |
| WO | 2017136785 | 8/2017 |

OTHER PUBLICATIONS

International Search Report dated Oct. 27, 2020, for related PCT application No. PCT/US2020/012961, filed Jan. 10, 2020. 12 pages.
European Search Report for related Application No. 16856348.4, dated Oct. 4, 2018.
PCT Search Report for related Application No. PCT/2017/016595, dated Feb. 3, 2017.
PCT Search Report for related Application No. PCT/2016/057196, dated Oct. 14, 2016.

* cited by examiner

COMPOSITIONS AND METHODS FOR HIGH EFFICIENCY PROTEIN PRECIPITATION

This application is a continuation of U.S. patent application Ser. No. 16/738,932, filed Jan. 9, 2020, now U.S. Pat. No. 10,815,270, which claims the benefit of U.S. Provisional Patent Application No. 62/903,644, filed on Sep. 20, 2019. These and all other referenced extrinsic materials are incorporated herein by reference in their entirety. Where a definition or use of a term in a reference that is incorporated by reference is inconsistent or contrary to the definition of that term provided herein, the definition of that term provided herein is deemed to be controlling.

FIELD OF THE INVENTION

The field of the invention is protein purification, in particularly from serum or plasma

BACKGROUND

The background description includes information that may be useful in understanding the present invention. It is not an admission that any of the information provided herein is prior art or relevant to the presently claimed invention, or that any publication specifically or implicitly referenced is prior art.

The non-cellular portion of human blood has long been used as a source of human proteins for therapeutic use (such as immunoglobulins, albumin, clotting factors, alpha 1 antitrypsin, etc.). Currently the most common source is blood plasma obtained from commercial donation centers. In order to be useful such proteins need to be isolated at high purity, while minimizing denaturation. In order to be successful, commercial endeavors need to recover these proteins in high yield by scalable processes. Unfortunately, these needs are often at odds with one another.

Protein purification processes typically include one or more precipitation steps, which are scalable and well suited for industrial processes. In such steps protein content of an aqueous solution is selectively precipitated (i.e. rendered insoluble) through the addition of a precipitant. For example, in Cohn fractionation ethanol is added to blood plasma in an amount sufficient to precipitate one or more protein species while leaving other proteins in solution. Such precipitation processes generate an insoluble protein precipitate and an aqueous-phase supernatant containing solvated proteins. These are subsequently separated (for example by centrifugation or filtration). Depending on the nature of the target protein and the concentration of the precipitant, either or both of the precipitate or the supernatant may be processed further to yield a purified target protein. However, in such precipitation steps the separation between insoluble and soluble proteins is rarely complete. Accordingly, some of the target protein present in the starting material will generally be lost to the non-collected fraction. Similarly, some contaminating proteins typically found in the non-collected fraction will generally be carried through into the collected fraction. In some instances the precipitant (e.g. ethanol), along with changes in pH, changes in temperature, and extended process times, can result in denaturation of a portion of the desired target protein.

The efficiency of such protein precipitation steps is a function of both precipitant concentration and the concentration of the protein of interest. Generally speaking, the efficiency with which a target protein is precipitated is inversely proportional to its concentration in the starting material solution. Accordingly, recovery of a desired protein as a precipitate can be reduced when it is present at low concentrations. Similarly, a potentially precipitable contaminating protein in the supernatant can be difficult to remove by precipitation if the starting concentration is relatively low. This problem is exacerbated by the common practice of introducing precipitants as stock solutions, which necessarily decreases the protein concentration of the reaction mixture. While the percentage of given protein precipitated from solution increases as the concentration of precipitant increases, selectivity decreases as the concentration of precipitant decreases.

Thus, there remains a need for a simple and effective method of improving the efficiency of protein precipitation.

SUMMARY OF THE INVENTION

The inventive subject matter provides methods for isolating proteins from complex mixtures by adding a precipitant at a low concentration and removing water from the resulting solution while retaining the precipitant, thereby simultaneously increasing protein and precipitant concentration.

One embodiment of the inventive concept is a method of isolating a protein from an aqueous solution (e.g. an intermediate from another protein separation process, a blood product, a cell culture media, a fermentation broth, a cell lysate, serum, plasma, cryo-poor plasma, redissolved cryoprecipitate), by adding a nonvolatile precipitant to an aqueous solution of proteins in an amount that provides a precipitant concentration that does not result in the formation of a precipitate. Water is removed from the resulting solution while retaining the precipitant until a concentration of the precipitant is reached that is sufficient to generate a protein-containing precipitate and a supernatant (which contains other proteins), followed by separation of the precipitate from the supernatant. The protein of interest can be recovered from the precipitate or the supernatant, depending on the nature of the protein, nature of the precipitant, and/or amount of precipitant. Suitable precipitants include, but are not limited to, organic acids, salts of organic acids (such as sodium citrate), inorganic salts, and hydrophilic polymers. Water can be removed by evaporation (for example, under reduced pressure), by ultrafiltration, or by any suitable method. In some embodiments additional water can be removed from the supernatant to generate a second precipitate and a second supernatant. In some embodiments supernatants from the method can be further subjected to a chromatography step. Similarly, precipitates from the method can be resolubilized and subjected to chromatography. Methods of the inventive concept can be used to isolate a variety of proteins, including (but no limited to fibrinogen, fibronectin, clotting factors, von Willebrand factor, an immunoglobulin, alpha-1 antitrypsin, and albumin.

Various objects, features, aspects and advantages of the inventive subject matter will become more apparent from the following detailed description of preferred embodiments, along with the accompanying drawing figures in which like numerals represent like components.

DETAILED DESCRIPTION

Figure 1:
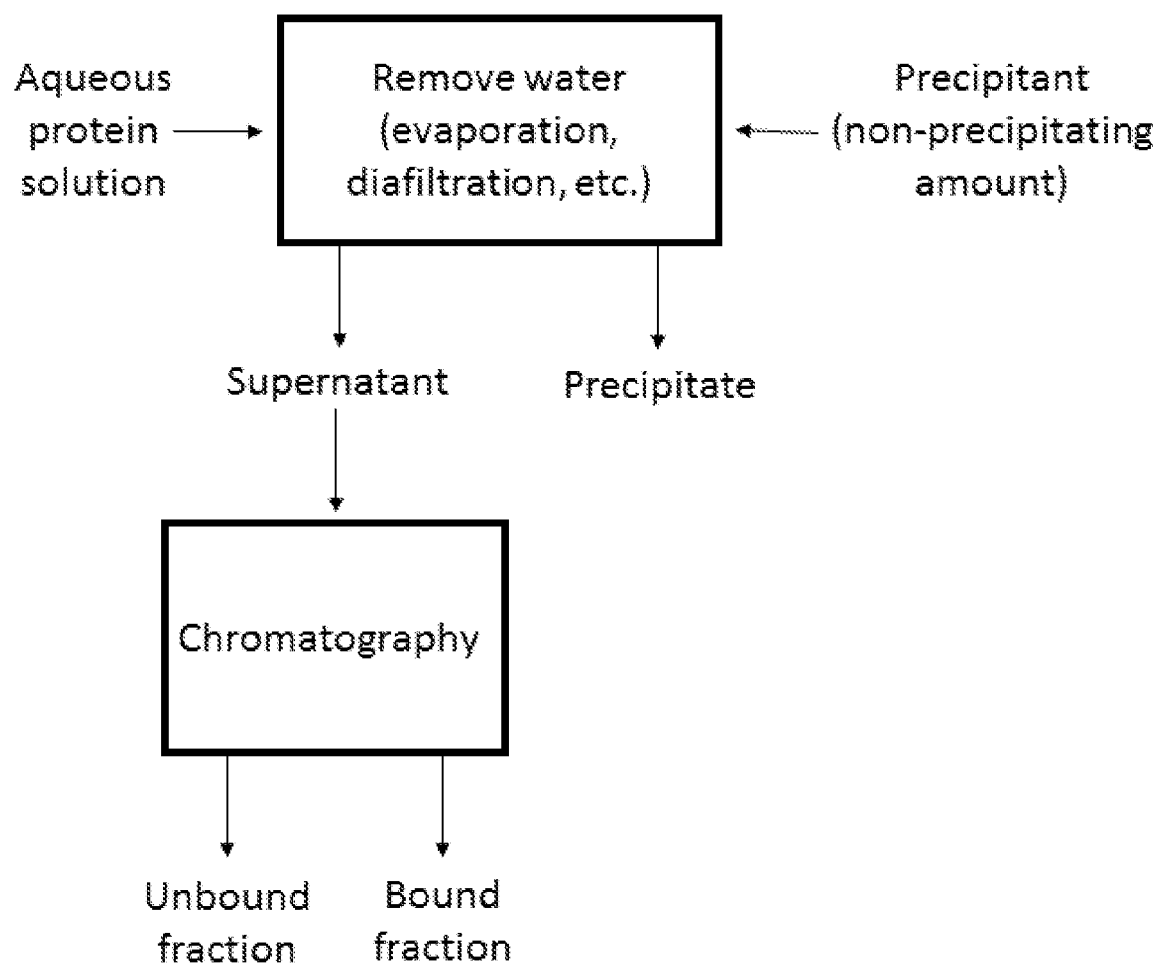
FIG. 1 schematically depicts an embodiment of a method of the inventive concept.

The following description includes information that may be useful in understanding the present invention. It is not an admission that any of the information provided herein is prior art or relevant to the presently claimed invention, or that any publication specifically or implicitly referenced is prior art.

In some embodiments, the numbers expressing quantities of ingredients, properties such as concentration, reaction conditions, and so forth, used to describe and claim certain embodiments of the invention are to be understood as being modified in some instances by the term "about." Accordingly, in some embodiments, the numerical parameters set forth in the written description and attached claims are approximations that can vary depending upon the desired properties sought to be obtained by a particular embodiment. In some embodiments, the numerical parameters should be construed in light of the number of reported significant digits and by applying ordinary rounding techniques. Notwithstanding that the numerical ranges and parameters setting forth the broad scope of some embodiments of the invention are approximations, the numerical values set forth in the specific examples are reported as precisely as practicable. The numerical values presented in some embodiments of the invention may contain certain errors necessarily resulting from the standard deviation found in their respective testing measurements.

As used in the description herein and throughout the claims that follow, the meaning of "a," "an," and "the" includes plural reference unless the context clearly dictates otherwise. Also, as used in the description herein, the meaning of "in" includes "in" and "on" unless the context clearly dictates otherwise.

The recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g. "such as") provided with respect to certain embodiments herein is intended merely to better illuminate the invention and does not pose a limitation on the scope of the invention otherwise claimed. No language in the specification should be construed as indicating any non-claimed element essential to the practice of the invention.

Groupings of alternative elements or embodiments of the invention disclosed herein are not to be construed as limitations. Each group member can be referred to and claimed individually or in any combination with other members of the group or other elements found herein. One or more members of a group can be included in, or deleted from, a group for reasons of convenience and/or patentability. When any such inclusion or deletion occurs, the specification is herein deemed to contain the group as modified thus fulfilling the written description of all Markush groups used in the appended claims.

The following discussion provides many example embodiments of the inventive subject matter. Although each embodiment represents a single combination of inventive elements, the inventive subject matter is considered to include all possible combinations of the disclosed elements. Thus, if one embodiment comprises elements A, B, and C, and a second embodiment comprises elements B and D, then the inventive subject matter is also considered to include other remaining combinations of A, B, C, or D, even if not explicitly disclosed.

The inventive concept provides compositions and methods in which a non-volatile precipitant (e.g. a sulfate salt, a phosphate salt, a salt of an organic acid, and or a soluble polymer) is introduced to an aqueous solution containing one or more target proteins and one or more contaminating proteins. An example of a method of the inventive concept is depicted schematically in FIG. 1. The precipitant is provided in an amount or a concentration that does not result in the formation of a visible precipitate. Water is then removed from the resulting reaction mixture to increase the concentration of both protein and precipitant simultaneously. When the protein concentration and precipitant concentration reach the desired target values a protein precipitate forms, and is subsequently separated from the supernatant fraction.

Depending on the nature of the target protein and the precipitant the target protein can be present in the precipitate or in the supernatant fraction. Since the protein concentration is increased as the precipitant concentration increases during this process the distribution of proteins between the precipitate and supernatant fractions can be different and distinct from that produced in conventional precipitation processes in which protein concentration is decreased or at best maintained as precipitant concentration increases. In some embodiments a supernatant obtained from such a precipitation process can be subjected to additional solvent (i.e. water) removal to further increase protein and precipitant concentration and generate a second precipitate and second supernatant fraction.

Simultaneously increasing protein concentration while increasing precipitant concentration in this fashion can improve the efficiency of precipitation, providing for increased yields of target proteins. In addition, initial introduction of the precipitant at concentrations that do not yield a visible precipitate precludes the formation of unwanted protein precipitants due to localized high concentrations of precipitant (as found on precipitant addition in conventional processes), decreasing the chance of undesirable protein denaturation and improving the specific activity of target proteins recovered from such processes.

As noted above, in embodiments of the inventive concept precipitants are selected to be nonvolatile (i.e. having a higher vapor pressure than water of the aqueous solution of protein under the current ambient condition). The amount of precipitant used can vary depending upon the nature of the precipitant. Suitable precipitants are preferably nondenaturing, and can include organic acids and salts of organic acids (e.g. sodium citrate), inorganic salts (e.g. ammonium sulfate, sodium sulfate, sodium chloride), and hydrophilic polymers (e.g. PEG, dextran, etc.). For example, if an organic salt such as sodium citrate is used it can be provided at concentrations ranging from about 0.1%, 0.2%, 0.5%, 1%, 2%, 3%, 4%, 5%, 6%, 7%, 8%, 9%, 10%, 12%, 15%, 18%, or less than about 20% (w/v). Similarly, if an inorganic salt such as ammonium sulfate is used it can be provided at concentrations ranging from about 0.1%, 0.2%, 0.5%, 1%, 2%, 3%, 4%, 5%, 6%, 7%, 8%, 9%, 10%, 12%, 15%, 18%, or less than about 20% (w/v). If a hydrophilic polymer such as PEG is used it can be provided at concentrations ranging from about 0.01%, 0.02%, 0.05%, 0.1%, 0.2%, 0.5%, 0.7%, 1%, 1.5%, 2%, 2.5%, 3%, 4%, 5%, 7% or less than about 10% (w/v).

Water can be removed from an aqueous solution of proteins containing a precipitant by any suitable method.

The method used can depend on the nature of the precipitant. For example, if the precipitant is a hydrophilic polymer filtration (e.g. ultrafiltration, diafiltration) utilizing a membrane with a molecular weight cutoff that is less than that of the molecular weight of the hydrophilic polymer can be used to remove water from the aqueous solution. In another embodiment, evaporation (at ambient pressure or at reduced pressure) can be used to remove water from the aqueous solution.

Any aqueous protein solution can serve as a starting material for methods and compositions of the inventive concept. Suitable aqueous protein solutions can include blood products (such as serum, plasma, cryo-poor plasma, and/or redissolved cryoprecipitate), lymphatic fluid, milk, urine, and/or egg contents. In other embodiments products of cell culture (e.g. mammalian, avian, insect, plant, and/or fungal cells) and/or microbial culture (such as cell culture media, fermentation broths, lysed mammalian, insect, avian, plant, fungal, bacterial, or fungal cells, etc.) can be used as an aqueous protein solution. In some embodiments the aqueous protein solution can be a process intermediate from a protein purification process, such as a chromatography column effluent, a peak eluted from a chromatography column, and/or a supernatant from a precipitation process.

Figure 2:
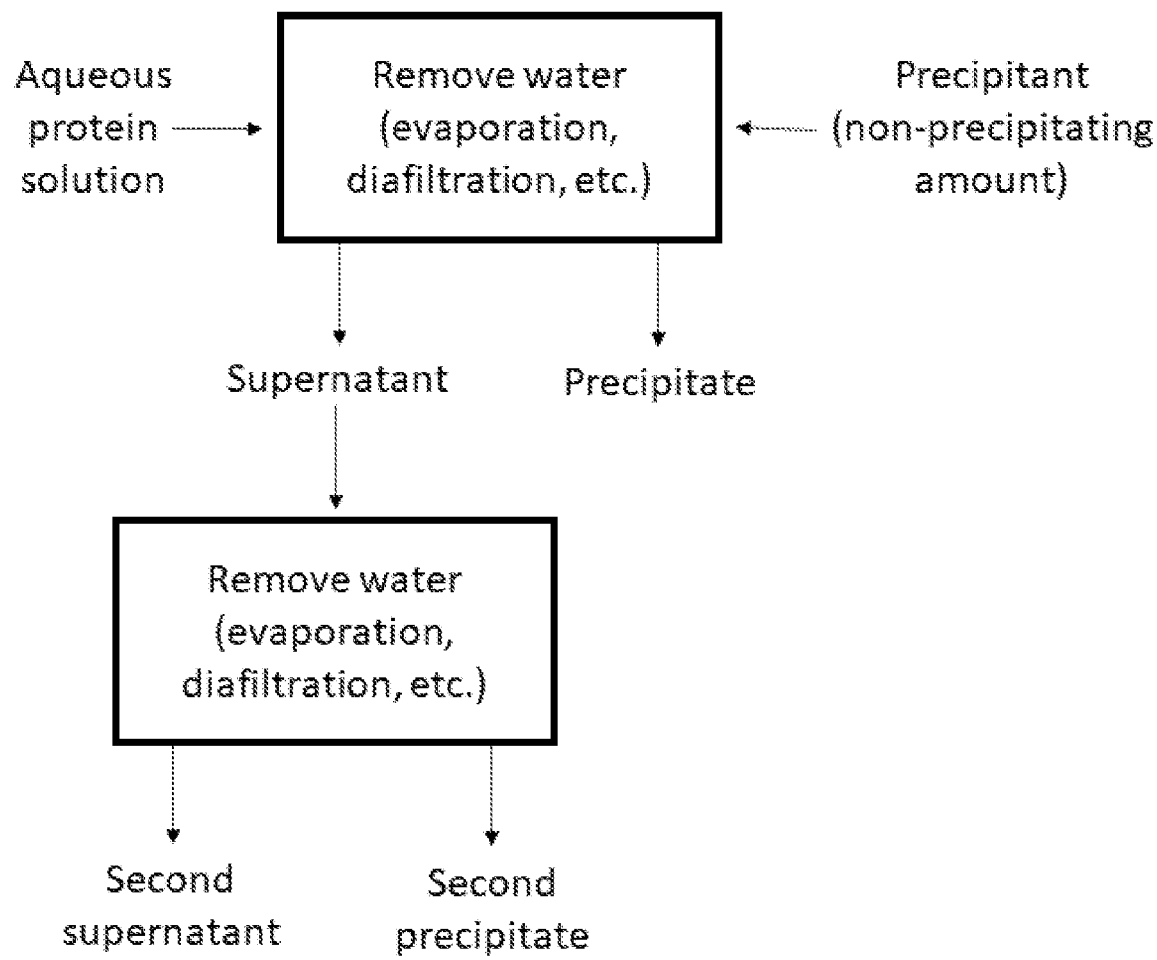
FIG. 2 schematically depicts an alternative embodiments of a method of the inventive concept.

In some embodiments of the inventive concept, a supernatant or a precipitate generated by a method of the inventive concept can be further processed to recover one or more target proteins and/or remove undesirable contaminants. In such embodiments a precipitate generated by the method can be redissolved prior to the additional processing. Suitable additional processing steps include further water removal from a supernatant to produce a second precipitate and second supernatant (see FIG. 2), conventional precipitation by addition of precipitating amounts of a precipitant, and/or chromatography (e.g. using ion exchange, hydrophobic interaction, affinity, mixed-mode, and or size exclusion chromatography media) of a supernatant generated by the method (see FIG. 1).

Chromatography media utilized in such additional processing can have any suitable formulation and configuration. Suitable media can be size exclusion, ion exchange, hydrophobic interaction, affinity, and/or mixed mode media. Suitable media can be provided as porous granules or beads, non-porous granules or beads, filters, fibers, and/or porous membranes. Structural portions of chromatography media can be based on any suitable materials. Examples include but are not limited to polysaccharides (such as cross-lined dextran), synthetic polymers, and/or inorganic materials (such as hydroxyapatite). Chromatography media can be provided in any suitable geometry. Suitable geometries include open or sealed chromatography columns, radial chromatography columns, cartridges, membrane housings, etc.

In an example of a method of the inventive concept, an aqueous protein solution (such as plasma) is obtained and blended with an equivalent volume of 8% (w/v) sodium citrate with rapid stirring, to form an aqueous protein solution with a non-precipitating sodium citrate concentration of 4% (w/v). The aqueous protein solution is transferred to a sealed container and the air pressure reduced to below that of the vapor pressure of water at the ambient temperature, resulting in the rapid evaporation of water from the solution. In some embodiments a small amount of air is continually bled into the sealed container during this process to prevent equilibration of the aqueous solution with water vapor inside the sealed chamber. Water is removed until the volume of the aqueous solution is reduced to bring the sodium citrate concentration to between about 10% and 12% while increasing the protein concentration, resulting in the formation of a visible precipitate. The precipitate can then be separated from the supernatant fraction, for example by filtration or by centrifugation. Such separation can be performed at ambient or reduced pressure.

In another example of a method of the inventive concept, an aqueous protein solution (such as plasma) is obtained and blended with an equivalent volume of 2% (w/v) polyethylene glycol (PEG) having a mean molecular weight of 5 kD using rapid stirring, to form an aqueous protein solution with a non-precipitating PEG concentration of 1% (w/v). The aqueous protein solution is subjected to ultrafiltration using a non-fouling membrane having a 3 kD molecular weight cutoff, resulting in the rapid removal of water and other low molecular weight species from the solution with retention of the PEG. Ultrafiltration is continued until the volume of the aqueous solution is reduced to about 25% of the original volume of the aqueous protein solution, bringing the PEG concentration to about 4% w/v while increasing the protein concentration and resulting in the formation of a visible precipitate. The precipitate can then be separated from the supernatant fraction, for example by filtration or by centrifugation.

When plasma, serum, or other blood products are the starting material a variety of pharmaceutically useful proteins can be obtained from methods of the inventive concept at high yield and specific activity. Such proteins include fibrinogen, factor VII, factor VIII, factor IX, factor XIII, von Willebrand factor, fibronectin, immunoglobulins, alpha-1 antitrypsin, protein C, protein S, C1 esterase inhibitor, antithrombin III, thrombin, and/or albumin.

It should be apparent to those skilled in the art that many more modifications besides those already described are possible without departing from the inventive concepts herein. The inventive subject matter, therefore, is not to be restricted except in the spirit of the appended claims. Moreover, in interpreting both the specification and the claims, all terms should be interpreted in the broadest possible manner consistent with the context. In particular, the terms "comprises" and "comprising" should be interpreted as referring to elements, components, or steps in a non-exclusive manner, indicating that the referenced elements, components, or steps may be present, or utilized, or combined with other elements, components, or steps that are not expressly referenced. Where the specification claims refer to at least one of something selected from the group consisting of A, B, C . . . and N, the text should be interpreted as requiring only one element from the group, not A plus N, or B plus N, etc.

What is claimed is:

1. A process intermediate generated from a first volume of source material, comprising, in a second volume, a first amount of solvated protein, a nonvolatile precipitant, and a second amount of precipitated protein, wherein the first amount and the second amount represent total protein content of the source material, wherein summation of the first amount and the second amount divided by the second volume is greater than total protein content of the source material divided by the first volume, wherein the process intermediate is derived from a process for isolating a desired protein from the source material and comprising adding the nonvolatile precipitant to the first volume of source material and removing solvent from the first volume of source material while retaining the nonvolatile precipitant and total protein content of the source material, so as to generate the second volume.

2. The process intermediate of claim 1, wherein the precipitant is selected from the group consisting of an organic acid, a salt of an organic acid, an inorganic salt, and a hydrophilic polymer.

3. The process intermediate of claim 1, wherein the precipitant is sodium citrate.

4. The process intermediate of claim 1, wherein the precipitant is a hydrophilic polymer.

5. The process intermediate of claim 1, wherein the source material is selected from the group consisting of a blood product, a cell culture media, a fermentation broth, and a cell lysate.

6. The process intermediate of claim 5, wherein the blood product is selected from the group consisting of a serum, a plasma, a cryo-poor plasma, and a redissolved cryoprecipitate.

7. The process intermediate of claim 1, wherein the source material is an intermediate from a protein separation process.

8. The process intermediate of claim 1, wherein the source material is selected to comprise at least one of fibrinogen, fibronectin, a clotting factor, von Willebrand factor, an immunoglobulin, alpha-1 antitrypsin, and albumin.

* * * * *